United States Patent
Fox

(10) Patent No.: US 7,074,312 B2
(45) Date of Patent: Jul. 11, 2006

(54) DEVICE FOR STACKING MULTIPLE PRE-CAST HORIZONTAL GELS

(75) Inventor: Gregory S. Fox, North Reading, MA (US)

(73) Assignee: Owl Separation Systems, Inc., Portsmouth, NH (US)

( * ) Notice: Subject to any disclaimer, the term of this patent is extended or adjusted under 35 U.S.C. 154(b) by 22 days.

(21) Appl. No.: 10/886,486

(22) Filed: Jul. 7, 2004

(65) Prior Publication Data

US 2006/0006069 A1    Jan. 12, 2006

(51) Int. Cl.
*G01N 27/447* (2006.01)
*G01N 27/453* (2006.01)

(52) U.S. Cl. ...................... 204/466; 204/616
(58) Field of Classification Search ........ 204/616–620, 204/466–467; 206/557, 558; 428/131, 136
See application file for complete search history.

(56) References Cited

U.S. PATENT DOCUMENTS

| | | | |
|---|---|---|---|
| 4,391,688 A | | 7/1983 | Hamelin ................. 204/461 |
| 5,232,573 A | * | 8/1993 | Rosenvold .............. 204/620 |
| 5,514,255 A | * | 5/1996 | Gautsch ................. 264/104 |
| 6,106,686 A | | 8/2000 | White et al. ............ 204/616 |
| 6,231,741 B1 | * | 5/2001 | Tuurenhout et al. ...... 204/618 |
| 6,689,267 B1 | * | 2/2004 | Audeh .................... 204/616 |

FOREIGN PATENT DOCUMENTS

WO    WO 9110901 A1 *  7/1991

OTHER PUBLICATIONS

How Can a Hippo ™ save You Space and Time?, Owl Separation Systems, 0402(7M) Lit. No. 15263, publication date unknown, one page description.*
Electro-4 Electro-phoresis System, Thermo Electron Corporation, publication date unknown, one page description.*

* cited by examiner

*Primary Examiner*—Alex Noguerola
(74) *Attorney, Agent, or Firm*—Andrus, Sceales, Starke & Sawall, LLP

(57) ABSTRACT

A device for vertically stacking multiple pre-cast gels for simultaneous electrophoresis is described. The device comprises a plate of non-electrically conductive material that separates adjacent gels within a vertical stack and facilitates contact between the ends of the gels and an electrolyte solution during electrophoretic separation procedures. Further, a method of using the device for simultaneous electrophoresis of multiple pre-cast gels is disclosed.

11 Claims, 7 Drawing Sheets

DEVICE FOR STACKING MULTIPLE PRE-CAST HORIZONTAL GELS

FIELD OF THE INVENTION

The present invention relates to devices for stacking multiple pre-cast gels for simultaneous electrophoresis within a horizontal electrophoresis system.

BACKGROUND OF THE INVENTION

Electrophoresis has become a popular method of analyzing, detecting, and/or purifying biological macromolecules. Separation of macromolecules generally is accomplished through the use of a gelled medium in the form of a tube gel or slab gel. When electrophoresis was introduced, gels were typically made within a laboratory just prior to performing the electrophoretic separation. However, over time, a number of commercial pre-cast gel products have become available. Pre-cast gels offer users operational ease and consistency from experiment to experiment, especially important to laboratories processing large numbers of samples. Because slab gels are generally quite fragile, many pre-cast gel products are packaged within tubs or trays with four sides and a removable top or covering, to support and protect the gel from stresses of shipment and storage. It is particularly convenient for the end-user, and therefore more marketable for the gel manufacturer, if the entire gel tray containing a pre-cast gel is suitable for use "as is", by simply placing the tray containing the gel into an electrophoresis device.

However, the use of pre-cast gel in a tray within an electrophoresis system presents challenges. Typically, pre-cast gels differ from ordinary "user-prepared" gels in that user-prepared gels often have "open" ends; that is to say, there is nothing between the top and bottom end-edges of the gel and the buffered electrolyte solution used for electrophoresis. Pre-cast gels require support during shipment and storage, and therefore, are bounded on all sides, including the ends, by the four walls of the tray, presenting a barrier between the top and bottom edges of the gel and the buffer solution. Therefore, a system for running multiple pre-cast gels must allow contact between the top surface of the gel and the buffered electrolyte solution at each end of the gel in such a way as to create a substantially uniform flow of current through the gel.

Although a few existing horizontal gel systems permit the simultaneous running of multiple slab gels, for example, the Opossum™ and Hippo™ systems sold by Owl Separation Systems, Inc. (Portsmouth, N.H.), and the Electro-4™ system sold by Thermo Electron Corporation (Waltham, Mass.), the systems were not developed for use with pre-cast gels and adapting them for such use is problematic. Some electrophoresis systems, such as the Opossum, are designed to hold multiple gels in a grid-like fashion within the same plane. Such a design is functional for use with small gels but cannot reasonably be made to fit more than about two large gels due to space and size constraints. Also, the Opossum accommodates user-prepared gels in open-ended casting trays and is not ideally suited, in terms of providing substantially uniform current flow, for the standard four-sided trays used to contain pre-cast gels.

Other systems, such as Hippo and Electro-4, permit vertical stacking of gels, eliminating the problem of counter space, but other issues remain. The stacking supports of these systems are designed to serve as casting trays for preparation of user-prepared gels, wherein the end edges of the prepared gels come into direct contact with the buffered electrolyte solution, and the side edges of the gel meet the sides of the tray portion of the stacking support. Because the stacking supports in these systems are a fixed size, they do not fit all sizes of pre-cast gels. Thus if the pre-cast gel is narrower in width than the tray portion of the stacking support such that the sides of the pre-cast gel do not meet the sidewalls, the gel can tilt to one side when the buffer solution is added to the system, preventing current from running parallel to the length of the gel and distorting the separation pattern. Moreover, existing stacking supports for vertically stackable systems have sidewalls significantly deeper than the depth of most pre-cast gels, creating a significant space above the gel for containing electrolyte buffer solution. Generally, electrophoretic separation is improved when the volume of electrolyte buffer solution across the top surface is kept at a minimum. In the event that extra thick pre-cast slab gels are used, a thickness greater than the fixed distance separating the shelves of the stacking support would make use of existing stacking support systems impossible. Thus, the existing stacking supports are not suitable for use with pre-cast gels of any size and especially when the pre-cast gel is of a different dimension than the stacking support. Further, the existing stacking supports limit the total number of gels in a particular stack to four.

Unfortunately, pre-cast gels cannot be simply stacked without separating supports, because the gels in the stack are in direct contact, obstructing the substantially uniform flow of electrical current through and over each gel and leading to distortion of resultant electrophoretic profiles. Therefore, a need exists for a device that permits the stacking of multiple pre-cast gels within electrophoresis systems and provides appropriate conditions for the substantially uniform flow of electrical current through each of the gels even if the gels within a stack are of different widths.

SUMMARY OF THE INVENTION

The invention in one aspect is directed to a support plate designed to separate adjacent gel trays containing pre-cast gels while allowing appropriate access of the gels to electrical current flow. In another aspect, the invention is directed to a method of using the support plates to facilitate simultaneous electrophoresis of two or more pre-cast horizontal slab gels by stacking the pre-cast gels vertically such that a support plate separates each gel in the stack to provide substantially uniform flow over the gels. In yet another aspect, the invention is directed to a method of using the support plates to stack pre-cast gels of different widths for performing simultaneous electrophoresis.

DETAILED DESCRIPTION OF THE DRAWINGS

Figure 1:
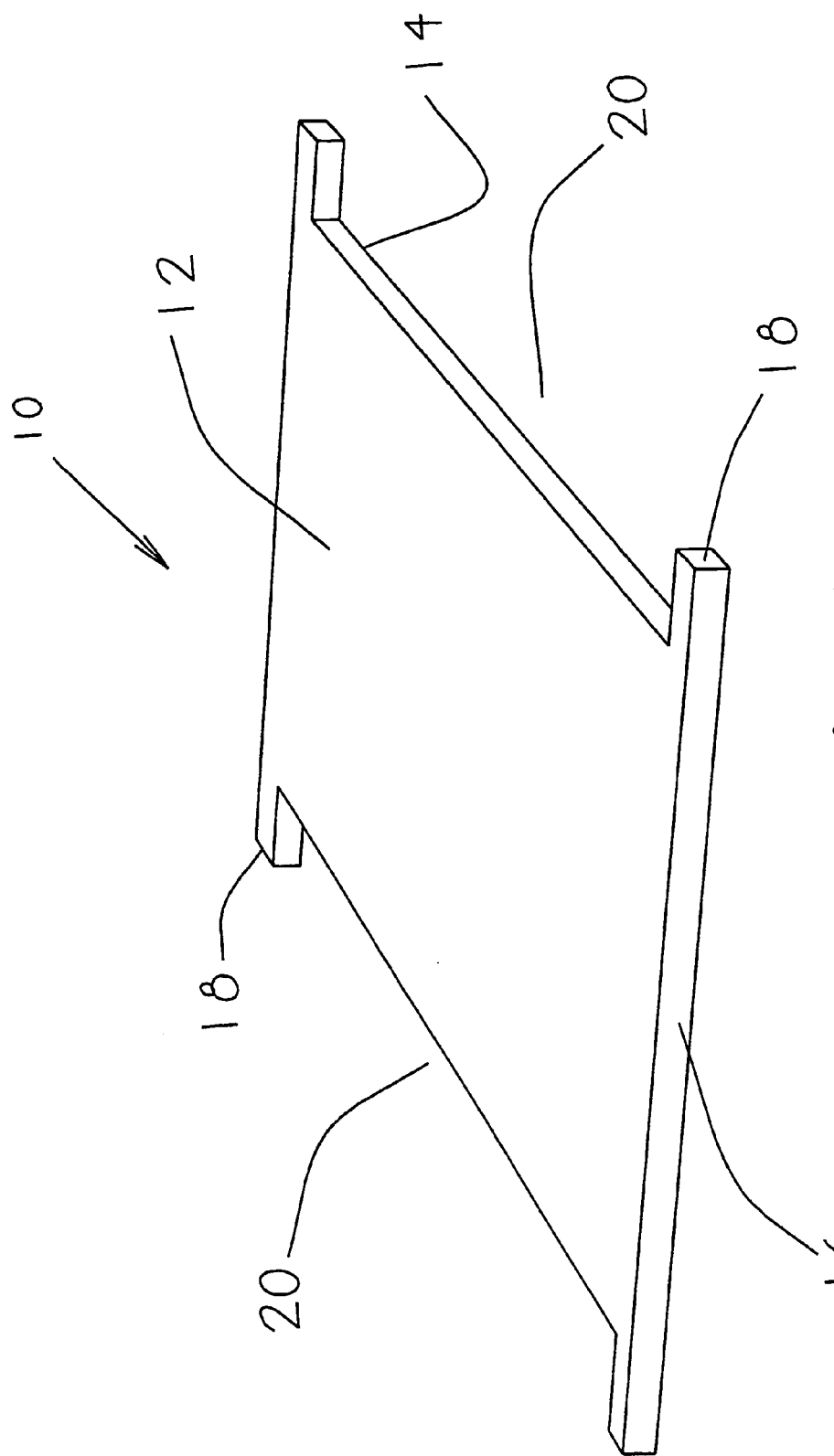
FIG. 1 is a perspective view of one embodiment of the separation plate of the present invention showing recessed areas at each of the opposed ends.

FIG. 1 shows a simple embodiment of a separation plate 10 of the present invention. The plate 10 is comprised of an electrically non-conductive material including, but not limited to, plastic polymer, glass, alumina or coated metals such as titanium or aluminum. The plate 10 has a substantially flat top surface 12 and bottom surface 14, with opposed sides 16 and opposed ends 18. Each opposed end 18 has a recessed area 20 to facilitate contact between the underlying gel and an electrolytic solution for electrophoresis when in use. Depending upon the electrically non-conductive material used, the plate 10 with its recesses 20 can be made via machine cutting and/or molding processes known in the art.

Alternatively, a simple rectangular plate without recesses can be used (not shown) as long as the width is at least as wide as the pre-cast gel to be covered and, wherein when gels remain within trays during electrophoresis, the length of the plate 10 is shorter than the length of the pre-cast gel tray so that each end of the gel is exposed for purposes of contacting an electrolytic solution. However, the length of the plate 10 should be sufficient to serve as a stable platform for any gel to be stacked on top of it so that there is no risk of the gel tilting at one end. In yet another embodiment, a simple rectangular plate 10 can be used to separate adjacent pre-cast gels within a vertical stack wherein the pre-cast gels are removed from their trays prior to electrophoresis or wherein the ends of the trays are designed in such a way as to allow contact between the end of the gels and the electrolyte solution used for electrophoresis.

Depending upon the electrically non-conductive material used, the thickness of the plate 10 can vary as long as the plate 10 has the required strength to support a pre-cast gel. For example, plate thickness for plastics can range from approximately 0.05 inches to 0.30 inches, with a thickness of approximately 0.125 inches particularly suited for plastic polymers to be injection molded, due to faster cooling times. Acrylics are typically sold as sheet stock in standard sizes to be machine cut. Generally, acrylic sheets sold at 0.125 inches in thickness is extruded and, thus, is composed of less desirable low molecular weight polymer; therefore, the 0.25 thick acrylic sheet, which is usually cast as opposed to extruded, is preferable for the purposes of the present invention. Coated metals, such as titanium and aluminum, can be used at a thickness equivalent to their lower manufacturing limits. Manufacturing properties of these standard materials are well known in the art.

Figure 2:
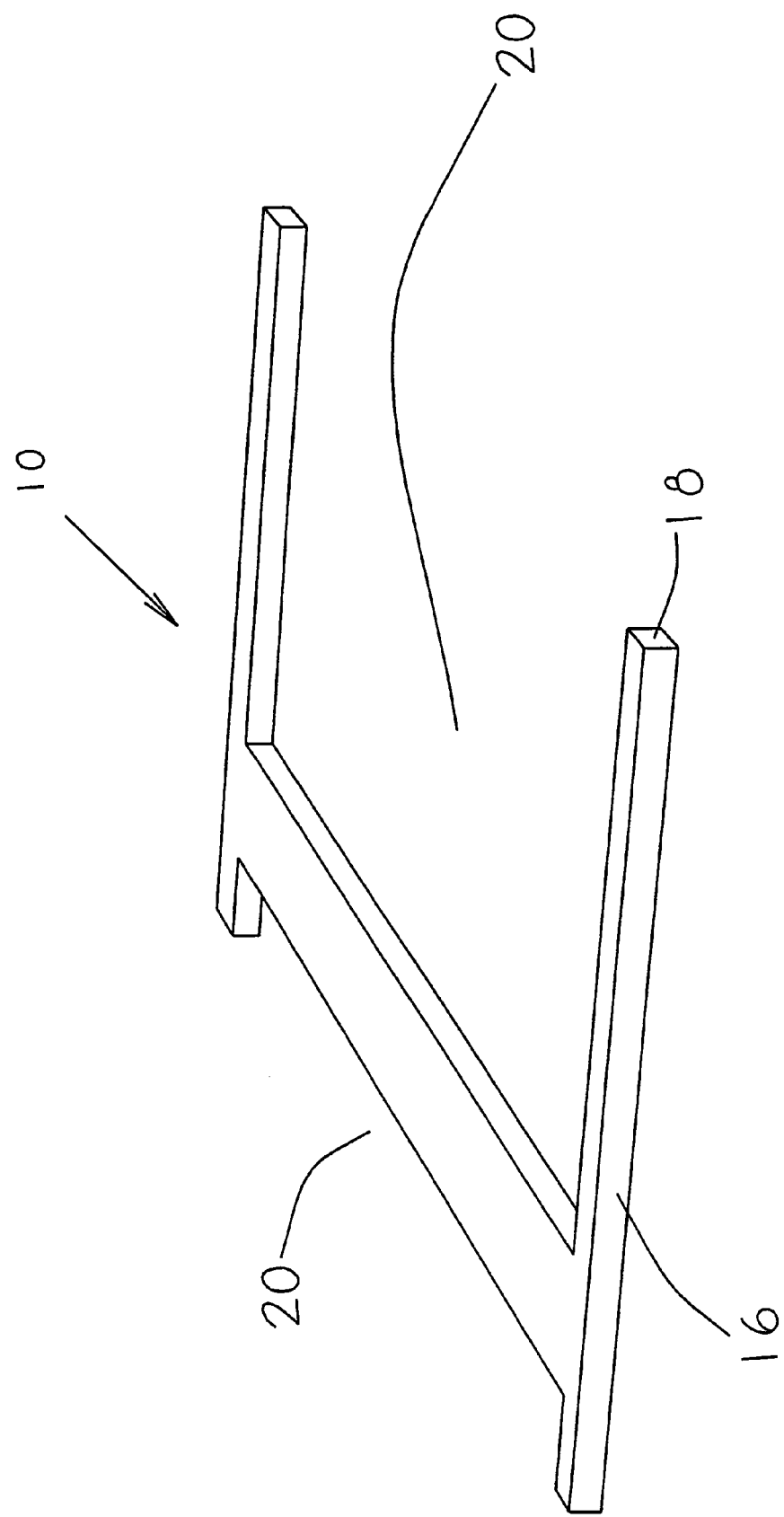
FIG. 2 is a perspective view of one embodiment of the separation plate wherein recessed areas are not equal in size to each other.

As shown in FIG. 2, the recesses 20 need not be of equal size. Such disproportionate recesses 20 are suitable for use with gels, for example, when multiple rows of sample wells exist within the same gel.

Figure 3:
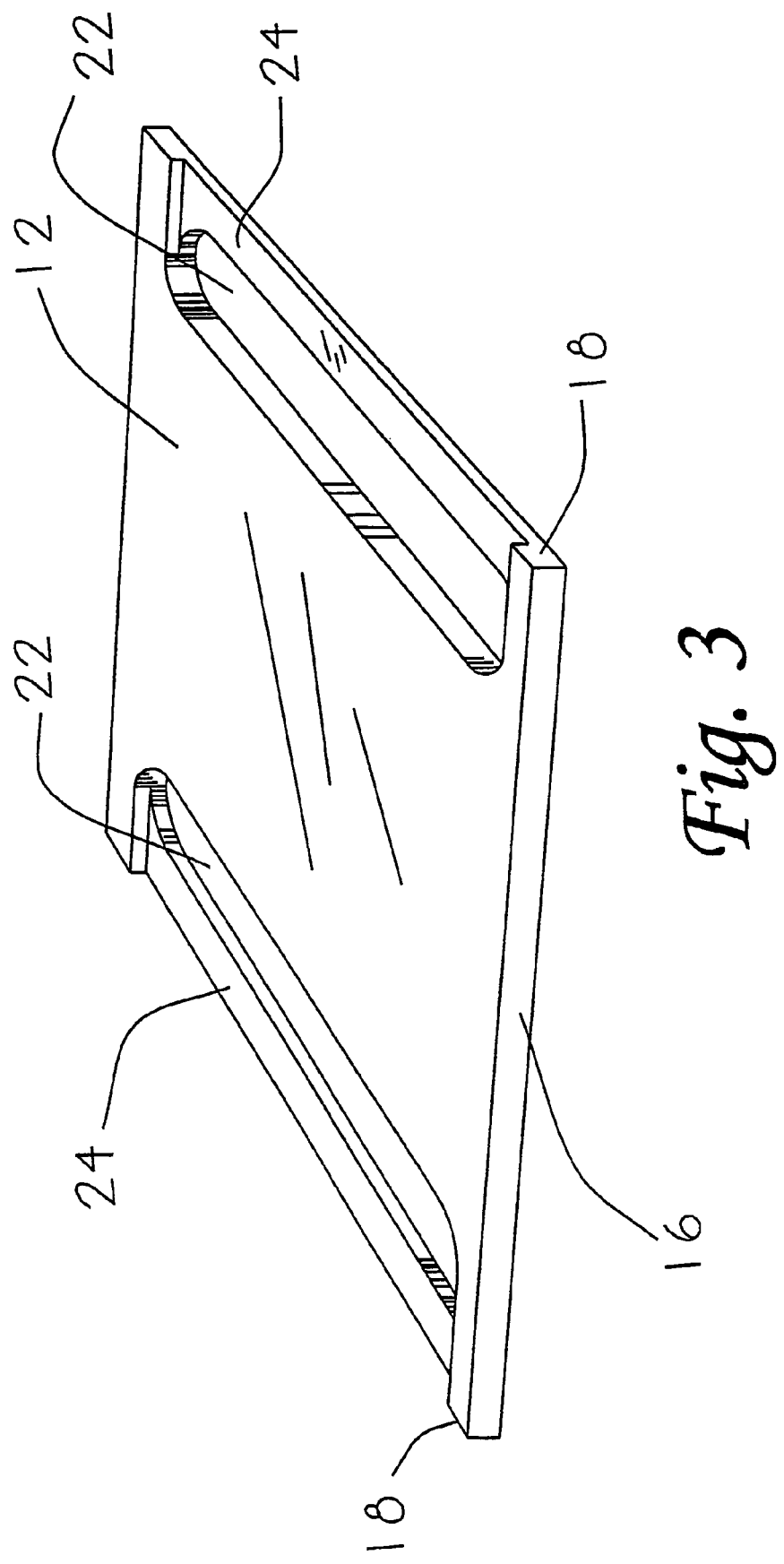
FIG. 3 is a perspective view of an embodiment of the separation plate with elongated apertures for facilitating contact between the ends of a gel and an electrophoresis solution.
Figure 4:
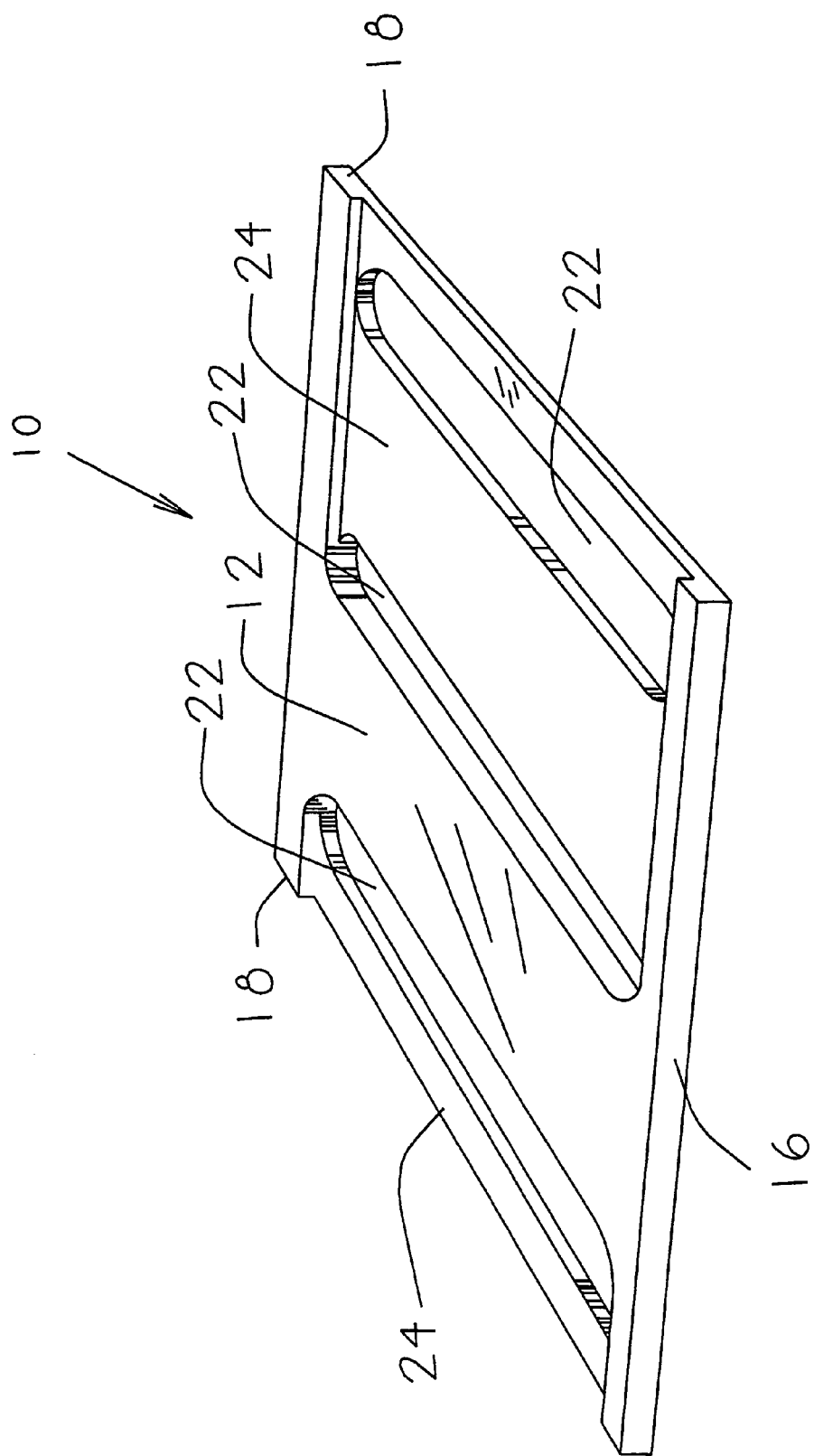
FIG. 4 is a perspective view of an embodiment of the separation plate of the present invention with an additional elongated aperture located between the end apertures.

Alternatively, instead of recesses 20, the plate 10 can be rectangular with elongated apertures 22 cut, molded or otherwise formed proximate to each end 18 as shown in FIG. 3. Preferably, in order for such apertures 22 to facilitate access to an electrolyte solution while the remainder of the plate 10 provides even blockage of electrical current, at least one facilitating portion 24 with reduced thickness compared to the remainder of the plate 10 is formed in the top surface 12 from the aperture 22 to the end 18 of the plate 10. Additional apertures 22 can be formed in the plate 10 for use with gels having multiple rows of sample wells as shown in FIG. 4. Preferably, when a plate 10 is formed with three or more apertures 22, the facilitating portion 24 is expanded to include the area between additional apertures 22 and the end 18 of the plate 10.

Figure 5:
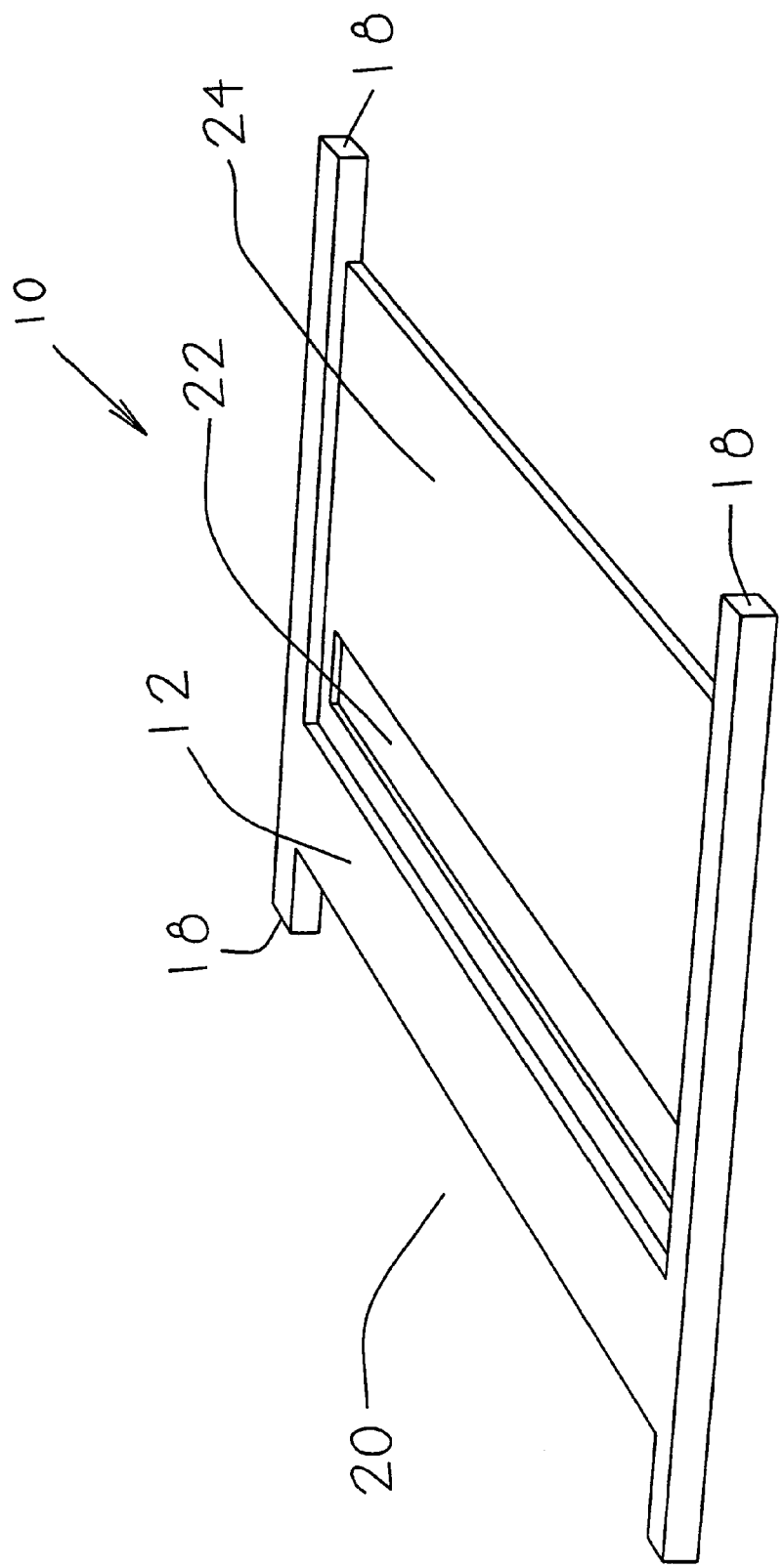
FIG. 5 is a perspective view of an embodiment of the separation plate of the present invention having a combination of apertures and a recessed end.

In yet another embodiment, shown in FIG. 5, combinations of a recess 20 and apertures 22 with a facilitating portion 24 can be used. Also, the dimensions of the plate 10 as formed can be varied to accommodate different sizes of pre-cast gels, in terms of length and/or width.

Figure 6:
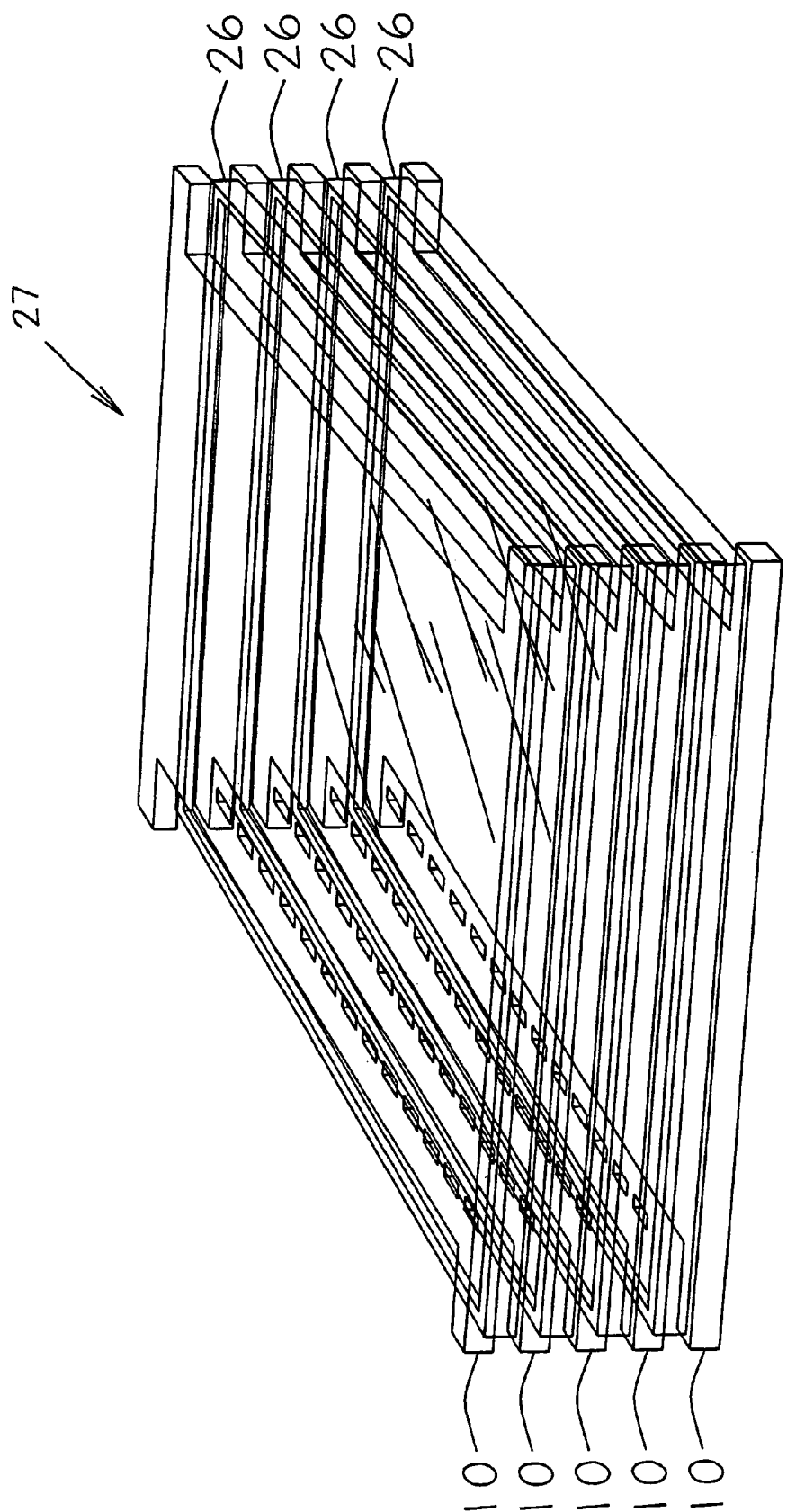
FIG. 6 is a perspective view of multiple pre-cast gels stacked vertically employing separation plates of the present invention.

FIG. 6 shows the use of separating plates 10 shown in FIG. 1 to vertically stack trays 26 containing pre-cast gels. A plate 10 is inserted between each tray 26 in the stack 27 and an additional plate 10 is placed on top of the stack 27, although use of a plate 10 on top of the stack 27 is optional. The number of gel trays 26 within a stack 27 is limited primarily only by the capacity of the electrophoresis system used and it may be possible to stack five or more gels for simultaneous electrophoresis. Another useful feature of the present invention is that trays 26 within a single stack 27 need not be of equal width since the width can vary as long as the separation plate 10 covering the top of a particular tray 26 is approximately at least as wide as the tray 26. Preferably, the samples to be electrophoretically separated are loaded within the gels prior to stacking.

Figure 7:
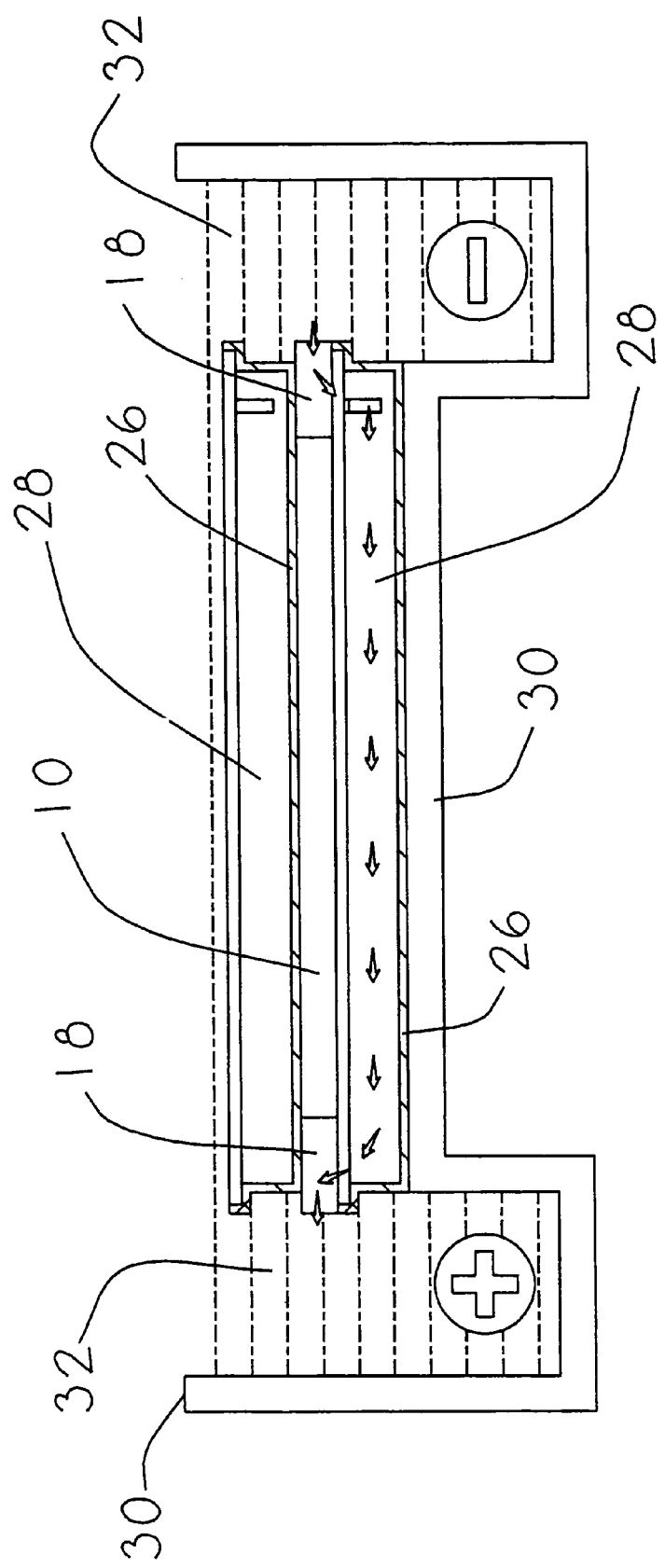
FIG. 7 is a cross-sectional view of a stack of pre-cast gels separated by a separation plate within a generic electrophoresis system.

In use, the stacked gels are contained within a single electrophoresis system 30, as shown in FIG. 7, so that the stacked gels 28 are electrophoresed simultaneously. Referring to the embodiment shown in FIG. 7, two pre-cast gels 28 are stacked and contained within a generic electrophoresis system 30. Viewed in cross-section, the plate 10 allows access of the electrolyte solution 32 to the gels 28 at each end 18. Such access permits current flow of electrical current through the gels 28 as indicated by the arrows. FIG. 7 shows the use of a separation plate 10 between each tray 26 without a plate 10 on top of the stacked gels 28; however, an additional plate 10 on top is preferred.

Other embodiments, modifications and alternatives may be apparent to those skilled in the art. Such embodiments, modifications and alternatives are considered to be within the spirit of the present invention.

I claim:

1. A device for separating pre-cast horizontal gels contained within gel trays wherein said gel trays are stacked vertically for simultaneous electrophoresis, the device comprising:

a substantially flat plate comprising an electrically non-conductive material;

said plate being approximately at least equal in width to said gel trays and comprising two opposed sides that are approximately at least equal in length to the length of said trays;

wherein two elongated apertures spanning substantially the width of said plate are located with one aperture proximate to each of the opposed ends of said plate such that the elongated apertures allow contact between the ends of the gel and a buffer solution for conducting electrical current; and at least one additional elongated aperture located in between the opposed ends of said plate, such that said at least one additional aperture allows contact between the gel and said buffer solution for conducting electrical current.

2. The device of claim 1 wherein said electrically non-conductive material is a plastic polymer, glass, alumina or coated metal.

3. The device of claim 1 wherein the thickness of said substantially flat plate is in a range from about 0.05 inches to about 0.30 inches.

4. The device of claim 1 wherein contact between the ends of the gel and a buffer solution for conducting electrical current is facilitated by an area of reduced thickness formed in the top surface of said plate from said elongated aperture to the end of said plate.

5. A method of performing simultaneous electrophoresis of two or more horizontal pre-cast gels comprising;
inserting a substantially flat plate comprising an electrically non-conductive material in between adjacent gels to form a vertical stack,
placing the entire stack within an electrophoresis unit, and performing electrophoresis,
wherein said plate is at least equal in width to said gel trays and comprises two opposed sides that are at least equal in length to the length of said trays, and opposed ends that are recessed inwardly of the ends of said pre-cast gel tray such that the recessed areas formed within said opposed ends of the plate are located between said opposed sides of said plate.
inserting a substantially flat plate comprising an electrically non-conductive material in between adjacent gels to form a vertical stack,
placing the entire stack within an electrophoresis unit, and performing electrophoresis,
wherein said plate is at least equal in width to said gels and comprises two opposed sides that are approximately equal in length to the length of said gels.

6. The method of claim 5 wherein an additional plate is placed on top of the entire stack prior to performing electrophoresis.

7. The method of claim 5 wherein five or more pre-cast gels are stacked vertically.

8. A method of performing simultaneous electrophoresis of two or more horizontal pre-cast gels comprising inserting a rectangular plate of an electrically non-conductive material in between adjacent gels to form a vertical stack, placing the entire stack within an electrophoresis unit, and performing electrophoresis.

9. The method of claim 8 wherein an additional plate is placed on top of the entire stack prior to performing electrophoresis.

10. The method of claim 8 wherein five or more pre-cast gels are stacked vertically.

11. A method of performing simultaneous electrophoresis of two or more horizontal pre-cast gels comprising.

* * * * *